(12) United States Patent
Stager (10) Patent No.: US 6,592,537 B2
(45) Date of Patent: Jul. 15, 2003

(54) WRISTPAD APPARATUS

(76) Inventor: Todd R. Stager, 1075 N. Miller, Bldg. #3, Apt. #267, Scottsdale, AZ (US) 85257

( * ) Notice: Subject to any disclaimer, the term of this patent is extended or adjusted under 35 U.S.C. 154(b) by 0 days.

(21) Appl. No.: 09/920,564

(22) Filed: Aug. 2, 2001

(65) Prior Publication Data
US 2003/0028136 A1 Feb. 6, 2003

(51) Int. Cl.[7] .................................................. A61F 5/00
(52) U.S. Cl. ........................ 602/21; 128/878; 128/879; 248/118
(58) Field of Search ................................ 602/20, 21, 5, 602/13, 62, 63, 64; 128/877, 878, 879; 248/118, 118.1, 118.5

(56) References Cited

U.S. PATENT DOCUMENTS

| | | | | |
|---|---|---|---|---|
| 5,827,207 A | * | 10/1998 | MacMorran | 602/21 |
| 6,048,325 A | * | 4/2000 | Kendall | 602/21 |
| 6,179,800 B1 | * | 1/2001 | Torrens | 602/21 |
| 6,213,969 B1 | * | 4/2001 | MacMorran | 602/64 |

* cited by examiner

Primary Examiner—Michael A. Brown (57) ABSTRACT

A wristpad apparatus includes a flexible wristband and a flexible pillow connected to the bottom wristband portion, either separably or permanently. With one embodiment, the wristband includes a plurality of wristband segments connected together with intersegment hinges. With other embodiments, a wristpad apparatus includes an inner wall and an outer wall, wherein a portion of the inner wall and the outer wall provide a flexible wristband, and wherein a portion of the inner wall and the outer wall define a first interwall chamber which contains a quantity of flexible filler material providing a flexible pillow. With another embodiment, the flexible wristband includes first and second wristband strap portions connect to each other when on a person's wrist. With another class of embodiments of the invention, a wrist pad apparatus includes a flexible pillow which includes wrist elevation adjustment means, e.g. water or air supplied through an attached valve assembly.

4 Claims, 7 Drawing Sheets

WRISTPAD APPARATUS

BACKGROUND OF THE INVENTION

1. Field of the Invention

The present invention relates generally to devices worn by a person using a computer keyboard and, more particularly, to devices especially adapted to support a person's wrist as the computer keyboard is used.

2. Description of the Prior Art

When persons spend extended times using a computer keyboard, it is well known that the person's wrists may be susceptible to fatigue. One reason for such fatigue is that generally the person's wrists are not supported as one types on the keyboard. To remedy this situation, throughout the years, a number of innovations have been developed relating to supporting a person's wrists as the person uses a computer keyboard, and the following U.S. patents are representative of some of those innovations: U.S. Pat. Nos. 5,161,760, 5,193,771, 5,228,655, 5,445,349, and 5,730,711. More specifically, U.S. Pat. No. 5,161,760 discloses wrist supports that are integrated into the structure of a computer keyboard. For purposes of simplicity and to permit a user to use virtually any existing keyboard, it would be desirable if a wrist support were provided that is not integrated into the structure of a keyboard.

U.S. Pat. No. 5,193,771 discloses a wrist support that includes an extension that extends under a portion of a person's palms. Such a device may impede raising and lowering of a person' hands with respect to the person's wrists. In this respect, it would be desirable if a wrist support were provided that which does not impede raising and lowering of person's hands as the person's wrists are being supported.

U.S. Pat. No. 5,228,655 discloses a wrist support that includes a portion that fits under a keyboard. As a result, the keyboard itself is raised when the wrist support is used. Clearly, the wrist support in this device is not independent of the keyboard. For purposes of simplicity and flexibility in using a wrist support, it would be desirable if a wrist support were provided that is independent of a keyboard.

U.S. Pat. No. 5,445,349 discloses a wrist support system that include a pillow that has a length equal to or greater than the length of the keyboard. Moreover, the pillow is not connected to a person's wrists. If person wanted to use another keyboard, such as on another computer, the person would have to carry the pillow to the other computer. In this respect, it would be desirable is a wrist support device were worn by a user.

U.S. Pat. No. 5,730,711 discloses a wrist support that can be worn by a user. In one embodiment, a wrist band is worn on a person's wrist, and a support pillow is located under the wrist band is connected to the wrist band by VELCRO(™) material. The wrist support pillow has a constant volume. Such a constant volume pillow is not readily adaptable to a wide variety hand sizes of a variety of users. In this respect, it would be desirable if a wrist support were provided which can have its pillow height adjusted to accommodate a wide variety of hand sizes of a variety of users.

Thus, while the foregoing body of prior art indicates it to be well known to use supports for peoples wrists using a keyboard, the prior art described above does not teach or suggest a wrist support for supporting a person's wrists when using a keyboard which has the following combination of desirable features: (1) is not integrated into the structure of a keyboard; (2) does not impede raising and lowering of a person's hands as the person's wrists are being supported; (3) is not connected to a keyboard; (4) is worn by a user; and (5) can have its pillow height adjusted to accommodate a wide variety of hand sizes of a variety of users. The foregoing desired characteristics are provided by the unique wristpad apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a wristpad apparatus which includes a flexible wristband which includes a top wristband portion and a bottom wristband portion. A flexible pillow is connected to the bottom wristband portion. The flexible pillow includes a flexible pillow housing. With one embodiment of the invention, the wristband includes a plurality of wristband segments connected together with intersegment hinges.

Each of the wristband segments includes flexible segment housings and a quantity of flexible, resilient segment filler material. The flexible segment housings and the intersegment hinges can be made from a common flexible material. The flexible segment housings, the intersegment hinges, and the pillow housing can be made from a common flexible material.

With another class of embodiments of the invention, a wristpad apparatus includes an inner wall and an outer wall, wherein a portion of the inner wall and the outer wall provide a flexible wristband, and wherein a portion of the inner wall and the outer wall define a first interwall chamber which contains a quantity of flexible filler material providing a flexible pillow.

With another embodiment of the invention, the inner wall includes a top inner wall portion and a bottom inner wall portion. The outer wall which includes a top outer wall portion and a bottom outer wall portion. The first interwall chamber is defined between the bottom inner wall portion and the bottom outer wall portion. A second interwall chamber is defined between the top inner wall portion and the top outer wall portion.

With another embodiment of the invention, the flexible wristband includes a first wristband strap portion which includes a first strap connector. A second wristband strap portion includes a complimentary second strap connector. Preferably, the first strap connector is made from a quantity of first hook-or-loop material, and the second strap connector is made from a quantity of complimentary second hook-or-loop material.

In accordance with another class of embodiments of the invention, a wristpad apparatus includes a flexible wristband which includes a top wristband portion and a bottom wristband portion. A flexible pillow is connected to the bottom wristband portion. The flexible pillow includes a flexible pillow housing and provides wrist elevation adjustment means.

In accordance with another embodiment of the invention, a valve assembly can be connected to the flexible pillow housing. The flexible pillow includes a quantity of fluid material contained within the flexible pillow housing supplied through the valve assembly. The fluid material can be water. The amount of water in the flexible pillow housing determines the adjusted height of the wearer's wrist.

More specifically, the flexible wristband includes an inner wristband wall and an outer wristband wall. The flexible pillow includes an inner pillow wall, and an outer pillow wall. The flexible pillow housing is defined by the inner pillow wall, and the valve assembly is connected to the inner pillow wall and the outer pillow wall.

In accordance with another embodiment of the invention, a wristpad apparatus includes a flexible wristband which includes a top wristband portion and a bottom wristband portion. The bottom wristband portion includes a bottom-mounted connector. A flexible pillow includes a top-mounted connector. The top-mounted connector is connectable with the bottom-mounted connector.

In accordance with another aspect of the present invention, a method is provided for making a wristpad apparatus which includes the steps of: obtaining a piece of double-plied material; bonding two edges of the piece of double-plied material, thereby forming a cylindrical shaped tube which has an inner wall and an outer wall, wherein the inner wall has a top inner wall portion and a bottom inner wall portion, and wherein the outer wall has a top outer wall portion and a bottom outer wall portion; separating the bottom inner wall portion from the bottom outer wall portion to form a first interwall chamber; and adding a quantity of cushioning material to the first interwall chamber.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least seven preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved wristpad apparatus which has all of the advantages of the prior art and none of the disadvantages.

It is another object of the present invention to provide a new and improved wristpad apparatus which may be easily and efficiently manufactured and marketed.

It is a further object of the present invention to provide a new and improved wristpad apparatus which is of durable and reliable construction.

An even further object of the present invention is to provide a new and improved wristpad apparatus which is susceptible of a low cost of manufacture with regard to both materials and labor, and which accordingly is then susceptible of low prices of sale to the consuming public, thereby making such wristpad apparatus available to the buying public.

Still yet a further object of the present invention is to provide a new and improved wristpad apparatus which is not integrated into the structure of a keyboard.

Still another object of the present invention is to provide a new and improved wristpad apparatus that does not impede raising and lowering of a person's hands as the person's wrists are being supported.

Yet another object of the present invention is to provide a new and improved wristpad apparatus which is not connected to a keyboard.

Even another object of the present invention is to provide a new and improved wristpad apparatus that is worn by a user.

Still a further object of the present invention is to provide a new and improved wristpad apparatus which can have its pillow height adjusted to accommodate a wide variety of hand sizes of a variety of users.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

With reference to the drawings, a new and improved wristpad apparatus embodying the principles and concepts of the present invention will be described.

Turning to FIGS. 1–6, there is shown a first embodiment of the wristpad apparatus of the invention generally designated by reference numeral 10. In the first embodiment, wristpad apparatus 10 includes a flexible wristband 12 which includes a top wristband portion 14 and a bottom wristband portion 16. A flexible pillow 18 is connected to the bottom wristband portion 16. Both the wristband 12 and the flexible pillow 18 include resilient material. The wristband 12 is comprised of flexible, resilient material so that the wristband 12 can stretch to fit a wide variety of wrist sizes.

The flexible pillow 18 includes a flexible pillow housing 24, and a quantity of inner, resilient pillow material 26 is contained inside the flexible pillow housing 24. The inner, resilient pillow material 26 is comprised of loose fibrous material. The inner, resilient pillow material 26 permits wrist elevation adjustment when the wristpad apparatus 10 is worn. The inner, resilient pillow material 26 can be POLYFIL(™) material.

The wristband 12 includes a plurality of wristband segments 20 connected together with intersegment hinges 22. Each of the wristband segments 20 includes a flexible segment housing and a quantity of flexible, resilient segment filler material. The flexible, resilient segment filler material can be POLYFIL(™) material. The flexible segment housings and the intersegment hinges 22 can be made from a common flexible material. In addition, the flexible segment housings, the intersegment hinges 22, and the pillow housing 24 can be made from a common flexible material. The common flexible material can be comprised of two-ply material having 78% cotton, 10% rubber, and 12% poly. The intersegment hinges 22 are comprised of flexible sheet material. In this respect, the intersegment hinges 22 can be so-called "living" hinges of plastic material. The top wristband portion 14 includes indicia 28. The indicia 28 can includes advertising material or an identifying logo.

Figure 1:
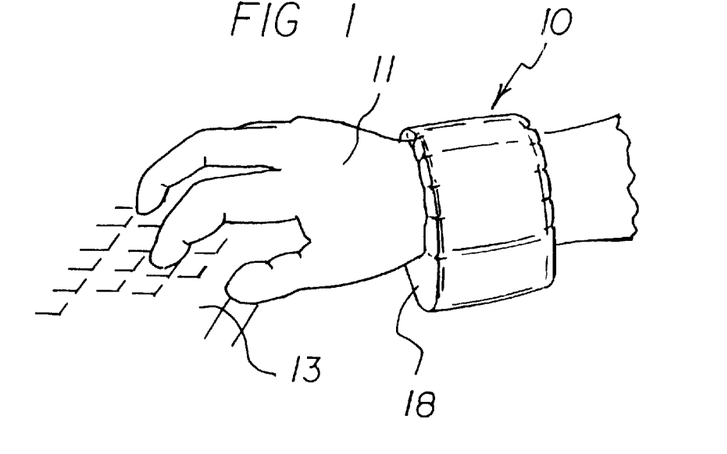
FIG. 1 is a perspective view showing a first embodiment of the wristpad apparatus of the invention being worn of a person's wrist as the person is using a keyboard.
Figure 2:
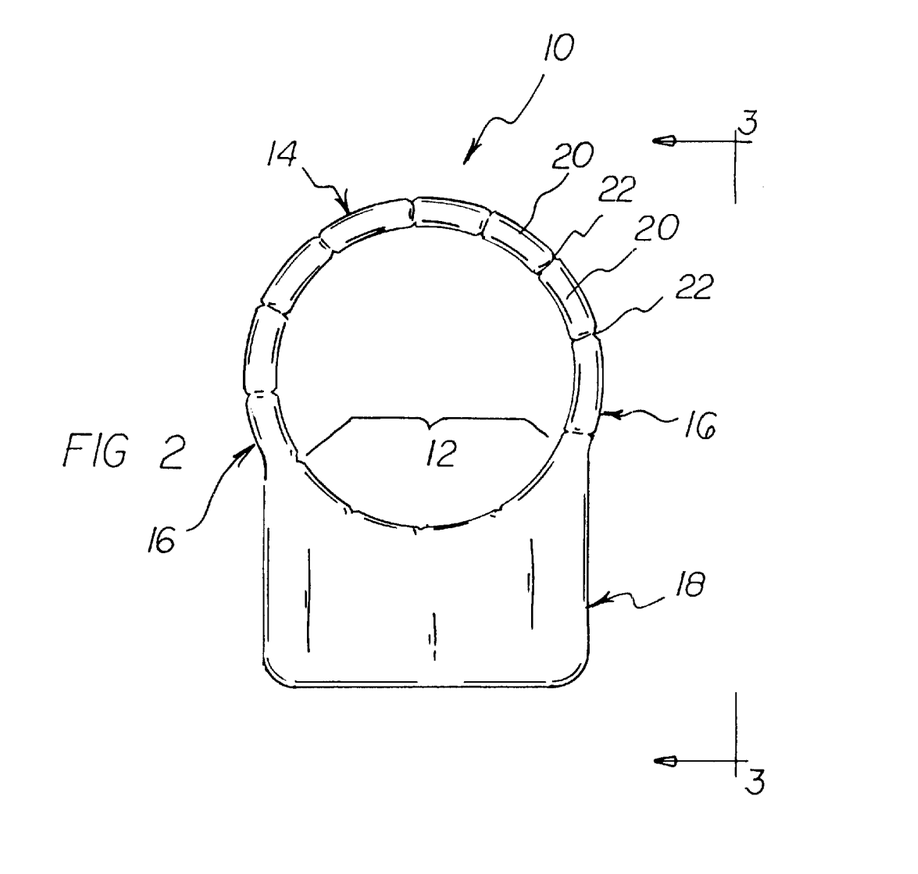
FIG. 2 is an enlarged front view of the embodiment of the wristpad apparatus shown in FIG. 1 removed from the person's wrist.
Figure 3:
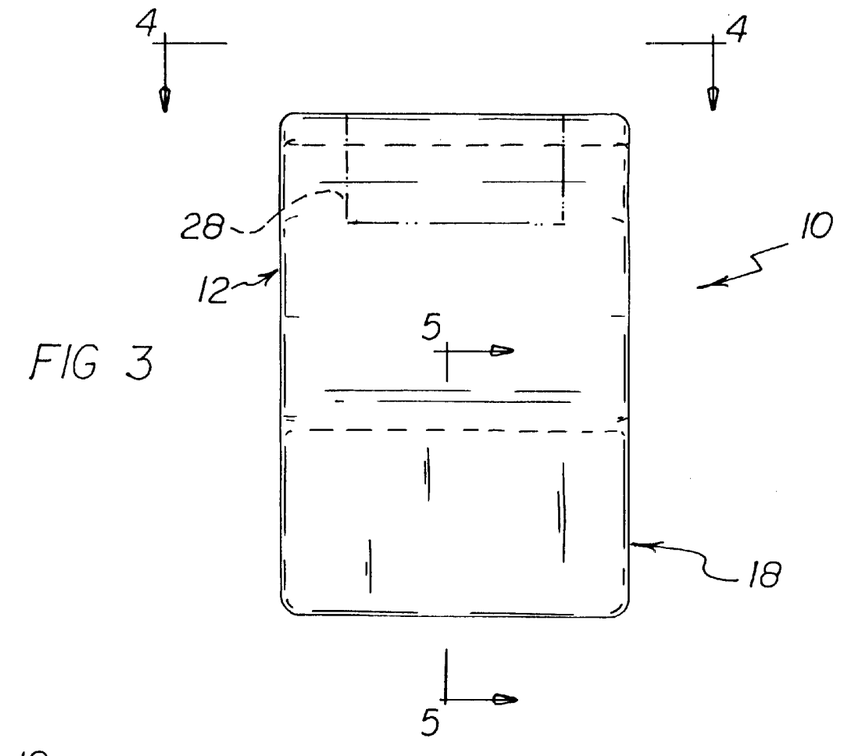
FIG. 3 is a side view of the embodiment of the wristpad apparatus of FIG. 2 taken along line 3—3 thereof.
Figure 4:
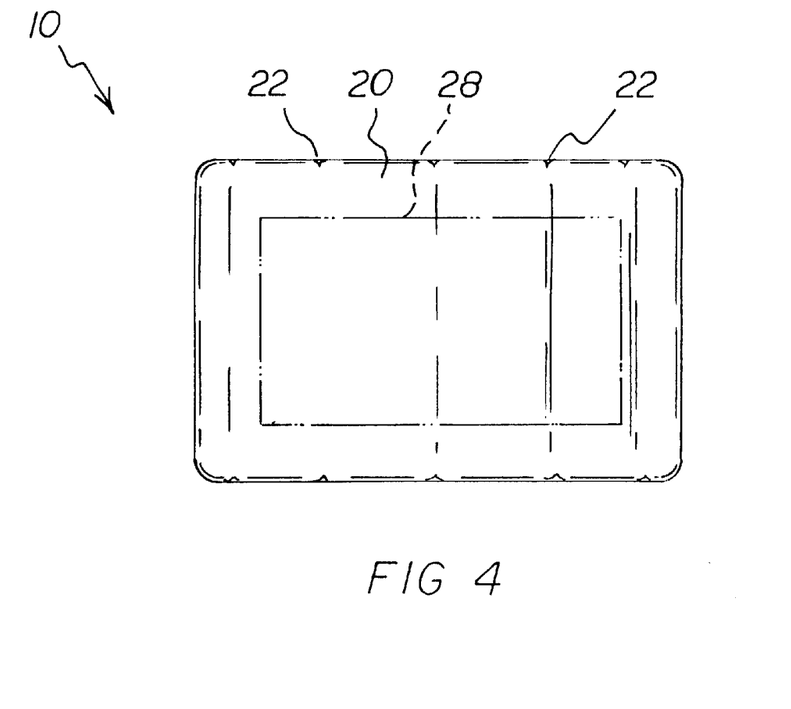
FIG. 4 is a top view of the embodiment of the invention shown in FIG. 3 taken along line 4—4 thereof.
Figure 5:
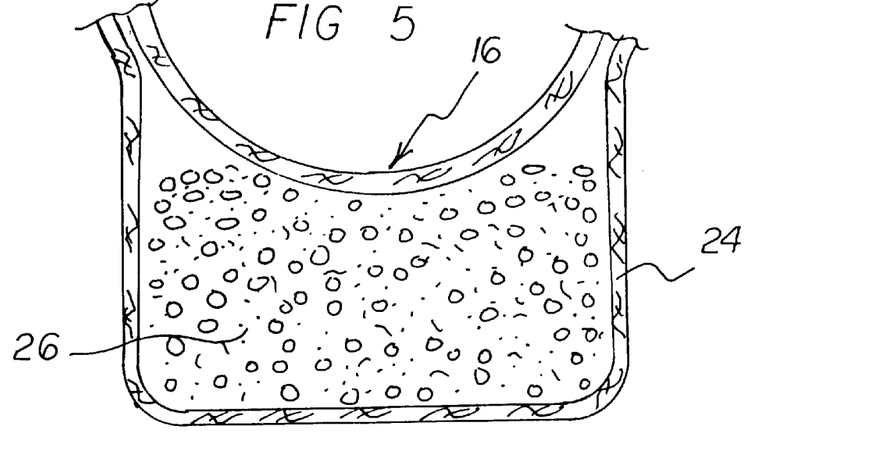
FIG. 5 is an enlarged partial cross-sectional view of the embodiment of the invention shown in FIGS. 3 taken along line 5—5 thereof.
Figure 6:
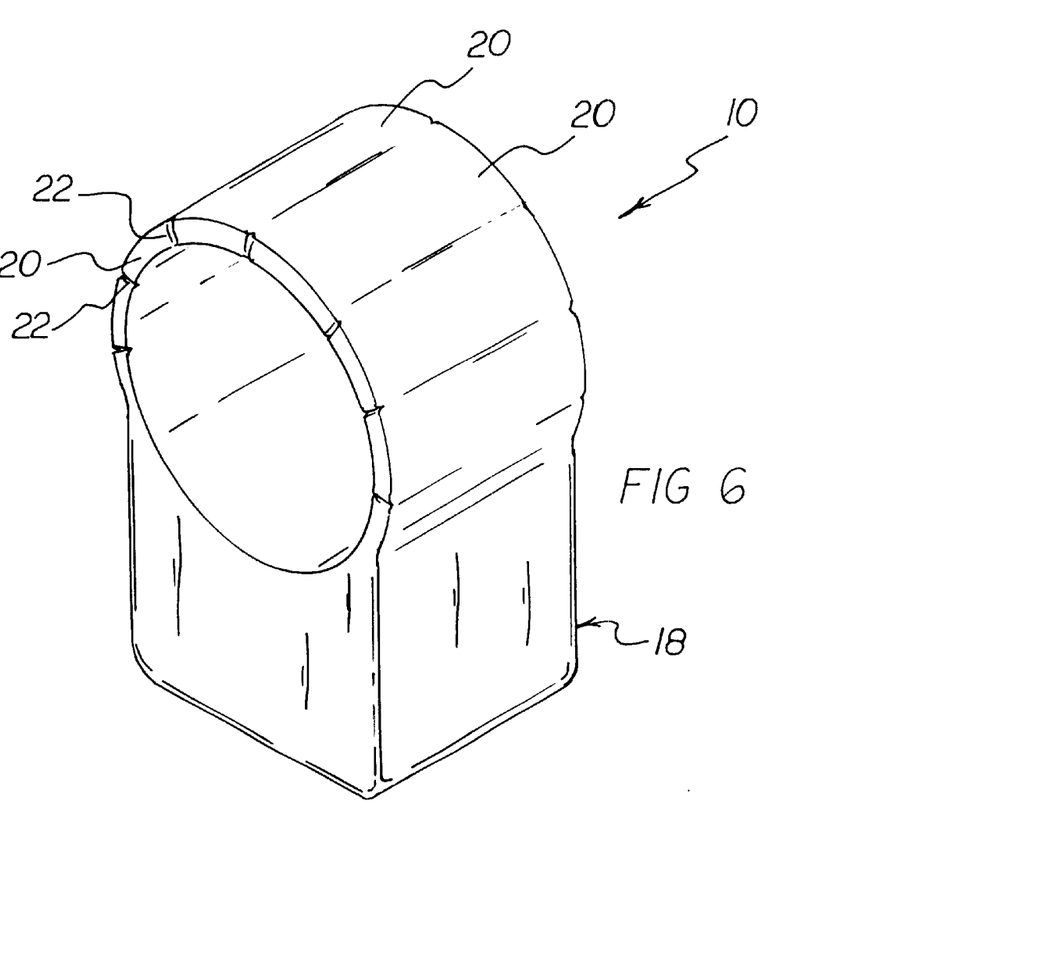
FIG. 6 is perspective view of the embodiment of the invention shown in FIGS. 1–5.

To use the wristpad apparatus 10 of the invention, a person pushes one's hand 11 to an opening provided in the wristband 12. The wristband 12 can stretch as the person's hand is pushed through, and, because of its resilient nature, contracts to fit snugly onto the person's wrist. The wristband 12 is positioned on the person's wrist, as shown in FIG. 1. Then, the person can type at a keyboard 13 with one's wrist resting on the flexible pillow of the wristpad apparatus 10.

The wristpad apparatus 10 of the invention is ergonomic, and when worn by a person, can increase a person's comfort when using a computer mouse, a keyboard, a ten-key, a typewriter, or a writing implement, especially when used for a long period of time. The wristpad apparatus 10 of the invention is lightweight, machine washable, portable, small in size, can be made in any color, and is imprintable by the use of silk screening, iron-ons, sewn-on labels, or embroidering.

In addition, the elevation of a person's wrist is adjustable when wearing the wristpad apparatus 10 of the invention by simply manipulating the contents, e.g. the POLYFIL(™), of the flexible pillow 18. To raise the elevation of a person's wrist when wearing the wristpad apparatus 10, portions of the contents of the flexible pillow 18 are pushed toward the center of the flexible pillow 18. This has the resultant effect of heightening the flexible pillow 18. In contrast, to lower the elevation of the person's wrist when wearing the wristpad apparatus 10, portions of the contents of the flexible pillow 18 are pushed to the sides of the flexible pillow 18. This has the effect of lowering the flexible pillow 18.

With another class of embodiments of the invention, a wristpad apparatus 10 includes an inner wall 26 and an outer wall 32, wherein a portion of the inner wall 26 and the outer wall 32 provide a flexible wristband, and wherein a portion of the inner wall 26 and the outer wall 32 define a first interwall chamber 38 which contains a quantity of flexible filler material providing a flexible pillow 18.

Figure 7:
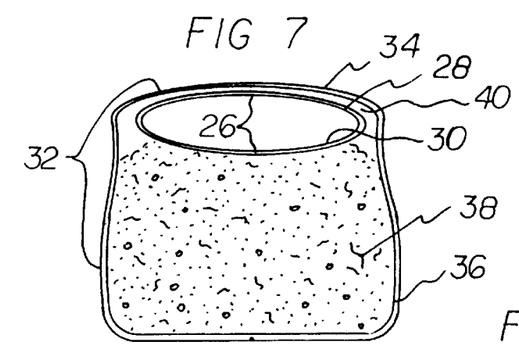
FIG. 7 is a cross-sectional view of a second embodiment of the invention formed from a double-ply material formed as a cylinder, wherein the flexible pillow portion is filled with relatively small size solid particulate material.

Turning to FIG. 7, a second embodiment of the invention is shown. Reference numerals are shown that correspond to like reference numerals that designate like elements shown in the other figures. In addition, the inner wall 26 includes a top inner wall portion 28 and a bottom inner wall portion 30. The outer wall 32 which includes a top outer wall portion 34 and a bottom outer wall portion 36. The first interwall chamber 38 is defined between the bottom inner wall portion 30 and the bottom outer wall portion 36. A second interwall chamber 40 is defined between the top inner wall portion 28 and the top outer wall portion 34. With this embodiment of the invention, the flexible pillow 18 includes small size solid particulate material, e.g. sawdust. With a preferred embodiment, the inner wall 26 and the outer wall 32 are comprised of a flexible, elastic, knitted fabric. If the first interwall chamber 38 is filled with small size solid particulate material, some of the small size solid particulate material can be manipulated from the first interwall chamber 38 to the second interwall chamber 40, if desired, in order to provide height adjustment for a person's wrist. If some small size solid particulate material were to be moved from the first interwall chamber 38 to the second interwall chamber 40, the elevation of the person's wrist would be decreased because less small size solid particulate material would be present in the first interwall chamber 38.

Figure 8:
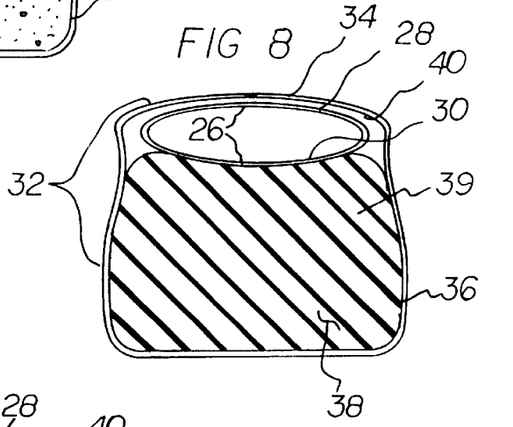
FIG. 8 is a cross-sectional view of a third embodiment of the invention formed from a double-ply material formed as a cylinder, wherein the flexible pillow portion is filled with a piece of solid foam material.

The third embodiment of the invention shown in FIG. 8 is similar to the embodiment of the invention shown in FIG. 7 except that the flexible pillow 18 is filled with a solid piece of foam material, e.g. foam rubber.

Figure 9:
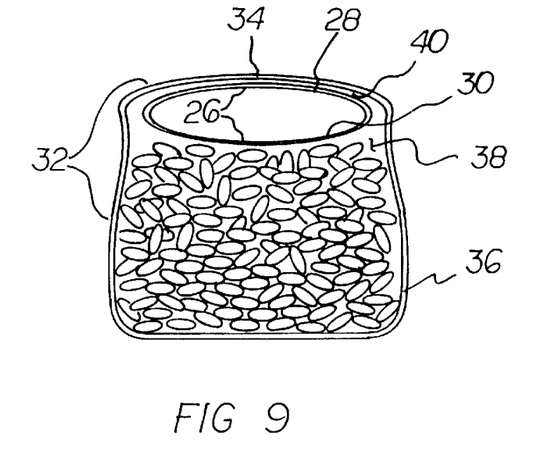
FIG. 9 is a cross-sectional view of a fourth embodiment of the invention formed from a double-ply material formed as a cylinder, wherein the flexible pillow portion is filled with relatively large size solid particulate material.

The fourth embodiment of the invention shown in FIG. 9 is similar to the embodiment of the invention shown in FIG. 7 except that the flexible pillow 18 is filled with large size solid particulate material, e.g. rice grains.

To make the second, third, fourth and seventh embodiments of the invention (the seventh embodiment being illustrated in FIGS. 14 and 15), a rectangular piece of double-plied material is obtained. If only single ply material is first available, then two single plies are bonded together, e.g. by sewing, to form double-plied material. The double-plied material has the property that the two plies of material can be separated from each other at desired portions. Two edges of the rectangular piece of double-plied material are sewn together to form a cylindrical shaped tube. As a result, the cylindrical shaped tube has a tubular inner wall 26 and a tubular outer wall 32. When viewed along the longitudinal axis of the cylindrical shaped tube, the inner wall 26 has a top inner wall portion 28 and a bottom inner wall portion 30. Also, when viewed along the longitudinal axis of the cylindrical shaped tube, the outer wall 32 has a top outer wall portion 34 and a bottom outer wall portion 36. See FIGS. 7–9. The bottom outer wall portion 36 can be separated from the bottom inner wall portion 30 to form the first interwall chamber 38. A small hole can be made in the bottom outer wall portion 36 to admit a quantity of particulate material into the first interwall chamber 38, such as done for the embodiments shown in FIGS. 7 and 9. Then, the small hole is sealed. Alternatively. A piece of foam rubber 39 can be admitted into the first interwall chamber 38.

Figure 14:
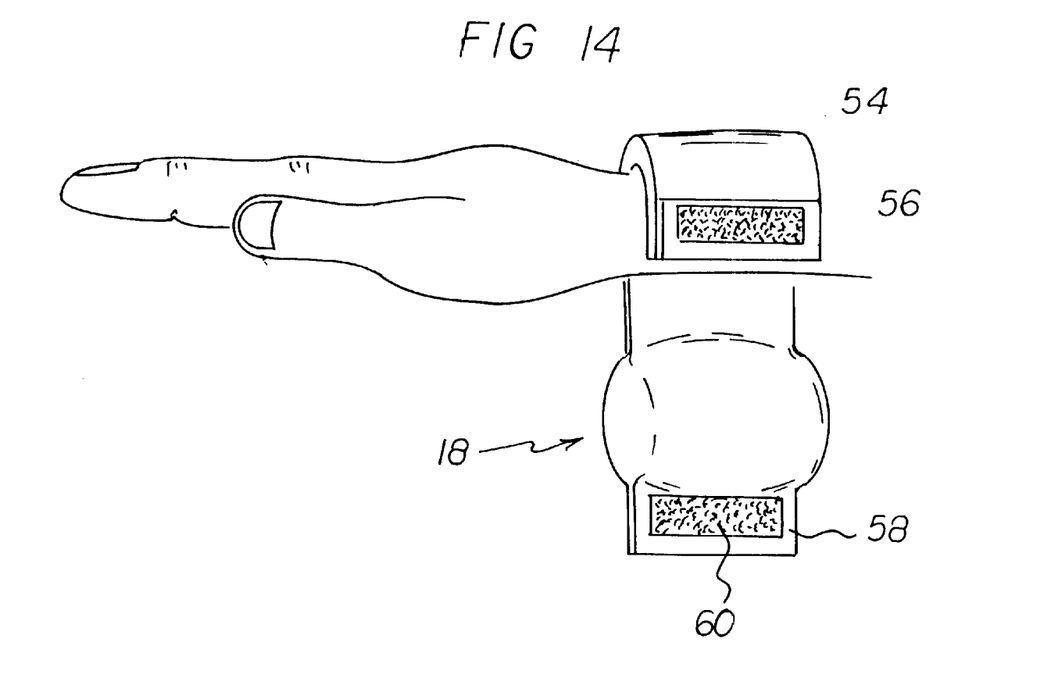
FIG. 14 is a side view of a seventh embodiment of the invention about to be secured to a wrist of a person, wherein the seventh embodiment of the invention includes a flexible pillow contained within a mid-portion of a quantity of double-ply material, and wherein the double-ply material includes free ends which are connectable together to form a flexible wristband.
Figure 15:
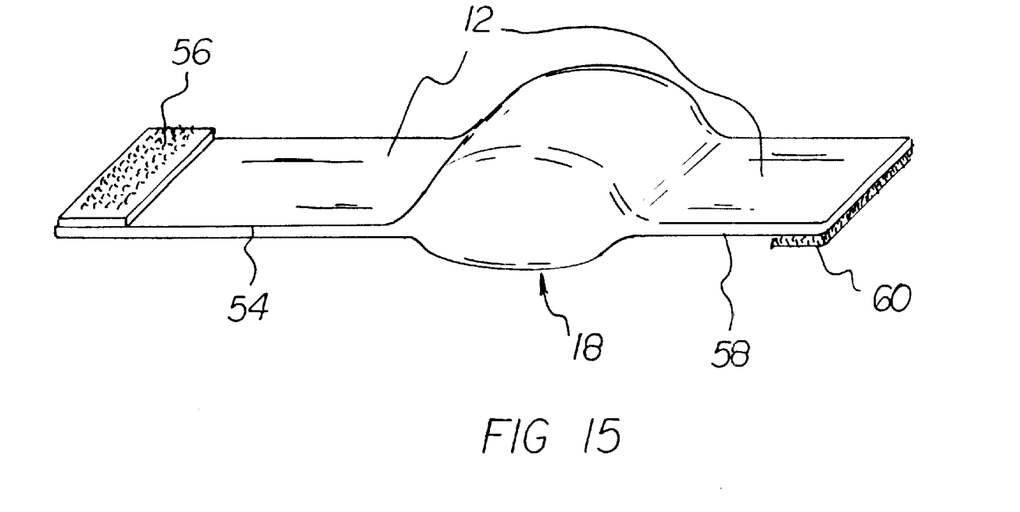
FIG. 15 is a perspective view of the seventh embodiment of FIG. 14 showing the wristband in a flattened condition prior to being secured to the wrist of a person.

In FIGS. 14 and 15, the seventh embodiment of the invention is shown. Reference numerals are shown that correspond to like reference numerals that designate like elements shown in the other figures. In addition, the flexible wristband 12 includes a first wristband strap portion 54 which includes a first strap connector 56. A second wristband strap portion 58 includes a complimentary second strap connector 60. Preferably, the first strap connector 56 is made from a quantity of first hook-or-loop material, the second strap connector 60 is made from a quantity of complimentary second hook-or-loop material. The first hook-or-loop material and the second hook-or-loop material can be made from well known VELCRO(™) material. Alternatively, the first strap connector 56 and the second strap connector 60 can include magnets, adhesives, buttons, snaps, zippers, clips, and latches, among other connecting means.

In accordance with another class of embodiments of the invention, a wristpad apparatus 10 includes a flexible wristband 12 which includes a top wristband portion 14 and a bottom wristband portion 16. A flexible pillow 18 is connected to the bottom wristband portion 16. The flexible pillow 18 includes a flexible pillow housing and provides wrist elevation adjustment means. Wrist elevation adjustment means are important for a number of reasons. Different people have different size hands, including different size fingers and different size palms. For a wristpad apparatus 10 of the invention that can be used by different people having different size hands, it is important that wrist elevation adjustment means are provided.

Figure 10:
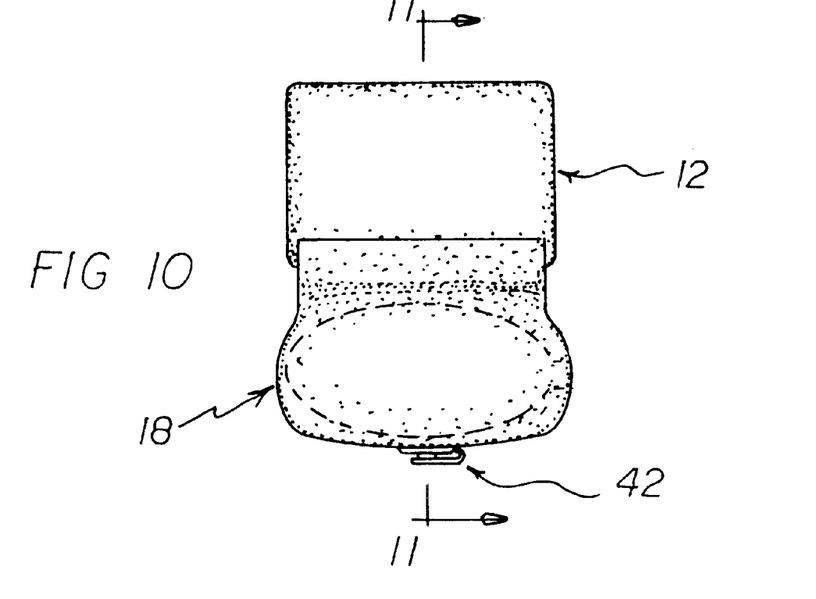
FIG. 10 is a side view of a fifth embodiment of the invention which includes a fluid reception bladder and a valve assembly for adding fluid to or removing fluid from the fluid reception bladder.
Figure 11:
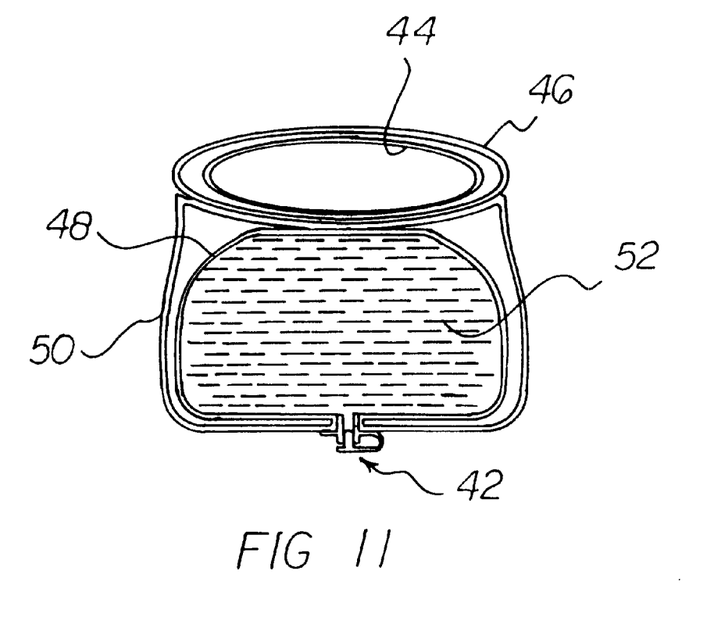
FIG. 11 is a cross-sectional view of the embodiment of the invention shown in FIG. 10 taken along line 11—11 thereof.

As shown in the embodiment of the invention illustrated in FIGS. 10 and 11, A valve assembly 42 can be connected to the flexible pillow housing. The flexible pillow 18 includes a quantity of fluid material contained within the flexible pillow housing supplied through the valve assembly 42. The fluid material can be water 52. The flexible wristband 12 is permanently adhered to the flexible pillow 18, such as by use of a quantity of adhesive material.

More specifically, the flexible wristband 12 includes an inner wristband wall 44 and an outer wristband wall 46. The flexible pillow 18 includes an inner pillow wall 48, and an outer pillow wall 50. The flexible pillow housing is defined by the inner pillow wall 48, and the valve assembly 42 is connected to the inner pillow wall 48 and the outer pillow wall 50. The flexible pillow housing defined by the inner pillow wall 48 defines a fluid reception bladder. The fluid reception bladder can be made from well known water-tight and/or air-tight materials.

By varying the quantity of water 52 contained in the fluid reception bladder, the height of the flexible pillow 18 can be adjusted. That is, when more water is added through the valve assembly 42 to the fluid reception bladder, a person's wrist is elevated more. When less water is added through the valve assembly 42 to the fluid reception bladder, the person's wrist is elevated less.

Figure 12:
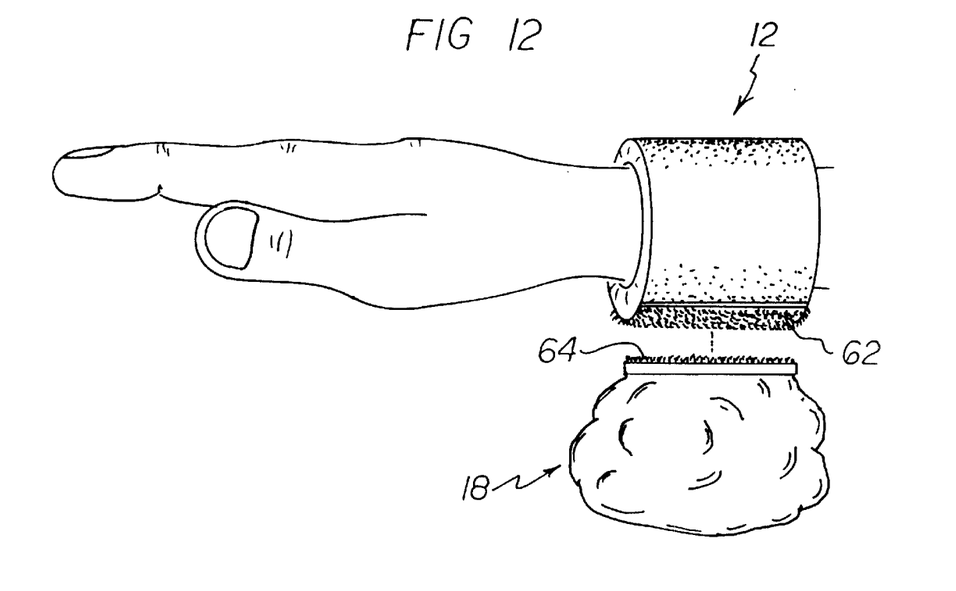
FIG. 12 is a partially exploded side view of a sixth embodiment of the invention, on the wrist of a person, wherein the sixth embodiment of the invention includes a separable flexible wristband and a separable flexible pillow which are connectable together using complimentary hook-and-loop material.
Figure 13:
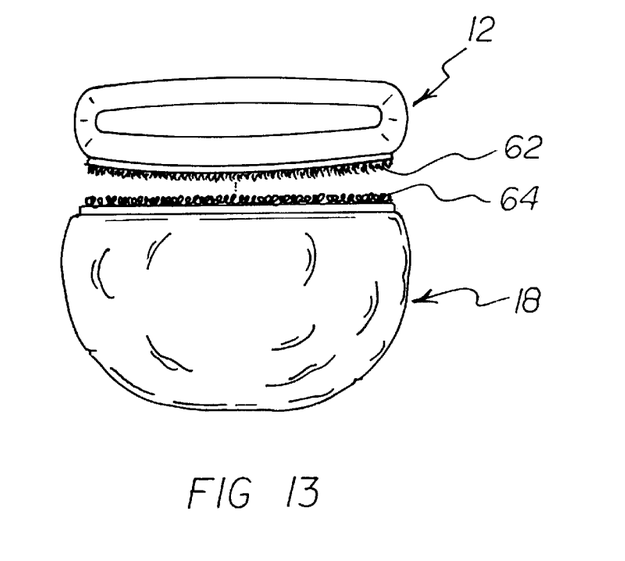
FIG. 13 is a partially exploded front view of the embodiment of the invention shown in FIG. 12.

In accordance with the sixth embodiment of the invention, a wristpad apparatus 10 includes a flexible wristband 12 which includes a top wristband portion 14 and a bottom wristband portion 16. The bottom wristband portion 16 includes a bottom-mounted connector 62. A flexible pillow 18 includes a top-mounted connector 64. The top-mounted connector 64 is connectable with the bottom-mounted connector 62. The bottom-mounted connector 62 and the top-mounted connector 64 can be made from well known VELCRO(™) material.

In accordance with another aspect of the present invention, a method is provided for making a wristpad apparatus 10 which includes the steps of: obtaining a piece of double-plied material; bonding two edges of the piece of double-plied material, thereby forming a cylindrical shaped tube which has an inner wall 26 and an outer wall 32, wherein the inner wall 26 has a top inner wall portion 28 and a bottom inner wall portion 30, and wherein the outer wall 32 has a top outer wall portion 34 and a bottom outer wall portion 36; separating the bottom inner wall portion 30 from the bottom outer wall portion 36 to form a first interwall chamber 38; and adding a quantity of cushioning material to the first interwall chamber 38.

Generally, the amount of cushioning material that is added to the first interwall chamber 38 determines the height of the flexible pillow 18 when the flexible pillow 18 is in use. When more cushioning material is added to the first interwall chamber 38. A person's wrist is elevated more. When less cushioning material is added to the first interwall chamber 38. A person's wrist is elevated less.

Generally, the flexible wristband 12 can be made from nylon, cotton, polyester, elastic, lycra, spandex, neoprene, silk, rayon, bandage material, or leather, and combinations thereof, among other materials. Generally, the flexible pillow 18 can contain a filler material that includes solid, liquid, or gaseous materials. Solid materials can include cotton, polyfil, plastic beads, styrofoam, rice, sawdust, seeds, dirt, clay, or gel materials, among other materials. Liquid materials can includes water. Gaseous materials can includes air.

With embodiments of the invention that employ a flexible wristband 12 which is separate and distinct from a flexible pillow 18 prior to assembly, the flexible wristband 12 and the flexible pillow 18 can be attached together by a number of means includes well known VELCRO(™) material, magnets, adhesives, button, snaps, zippers, clips, and latches, among other connecting means.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved wristpad apparatus that is low in cost, relatively simple in design and operation, and which may advantageously be used without being integrated into the structure of a keyboard. With the invention, a wristpad apparatus is provided which does not impede raising and lowering of a person's hands as the person's wrists are being supported. With the invention, a wristpad apparatus is provided which is not connected to a keyboard. With the invention, a wristpad apparatus is provided which is worn by a user. With the invention, a wristpad apparatus is provided which can have its pillow height adjusted to accommodate a wide variety of hand sizes of a variety of users.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A wristpad apparatus, comprising:
    a flexible wristband which includes a top wristband portion and a bottom wristband portion, each of said top wristpad portion and said bottom wristpad portion having a common longitudinal extent corresponding to the wrist region of a person,
    a flexible pillow connected to said bottom wristband portion, wherein said flexible pillow includes a flexible pillow housing, said flexible pillow housing further including resilient pillow material therein,
        wherein said wristband is a flexible, stretchable material comprising a plurality of wristband segments connected together with intersegment hinges, and
        wherein said flexible pillow housing has a longitudinal extent defined by the longitudinal common longitudinal extent of said top wristpad portion and said bottom wristpad portion.

2. The apparatus of claim 1 wherein each of said wristband segments includes:
    flexible segment housings, and
    a quantity of flexible, resilient segment filler material.

3. The apparatus of claim 2 wherein said flexible segment housings and said intersegment hinges can be made from a common flexible material.

4. The apparatus of claim 2 wherein said flexible segment housings, said intersegment hinges, and said pillow housing can be made from a common flexible material.

* * * * *